(12) United States Patent
Abraham et al.

(10) Patent No.: US 11,163,073 B2
(45) Date of Patent: Nov. 2, 2021

(54) CHARGER INTEGRATION-BASED VIRTUAL CT DETECTOR

(71) Applicant: ANALOGIC CORPORATION, Peabody, MA (US)

(72) Inventors: Douglas Abraham, Topsfield, MA (US); David Rozas, Brighton, MA (US)

(73) Assignee: Analogic Corporation, Peabody, MA (US)

( * ) Notice: Subject to any disclaimer, the term of this patent is extended or adjusted under 35 U.S.C. 154(b) by 375 days.

(21) Appl. No.: 16/129,905

(22) Filed: Sep. 13, 2018

(65) Prior Publication Data

US 2020/0088891 A1 Mar. 19, 2020

(51) Int. Cl.
| | |
|---|---|
| *A61B 6/00* | (2006.01) |
| *G01T 1/17* | (2006.01) |
| *A61B 6/03* | (2006.01) |
| *G01N 23/046* | (2018.01) |

(52) U.S. Cl.
CPC ............ *G01T 1/17* (2013.01); *A61B 6/035* (2013.01); *A61B 6/4266* (2013.01); *G01N 23/046* (2013.01)

(58) Field of Classification Search
CPC ..... A61B 6/035; A61B 6/4266; G01N 23/046
See application file for complete search history.

(56) References Cited

U.S. PATENT DOCUMENTS

| 6,078,638 A * | 6/2000 | Sauer et al. ........... A61B 6/032 378/4 |
| 9,057,788 B2 | 6/2015 | Abraham et al. |

* cited by examiner

*Primary Examiner* — Dani Fox
(74) *Attorney, Agent, or Firm* — TraskBritt (57) ABSTRACT

Among other things, one or more techniques and/or systems are described for creating virtual channels in an imaging modality. The imaging modality comprises a plurality of charge integrating channels. Information yielded from two or more charge integrating channels during a same or similar acquisition view may be combined to yield a virtual channel that represents a portion of the detection surface substantially equivalent to an area comprised by the two or more charge integrating channels. In one embodiment, within a same acquisition view, some virtual channels may comprise a different number of charge integrating channels than other virtual channels. Also, different sets of virtual channels may be created for a same acquisition view to produce different images from a single set of data, for example, where there may be overlap between virtual channels such that the same charge integrating channel is comprised in more than one virtual channel.

20 Claims, 5 Drawing Sheets

CHARGER INTEGRATION-BASED VIRTUAL CT DETECTOR

TECHNICAL FIELD

The present disclosure relates to the field of imaging modalities. It finds particular application to imaging modalities that can employ charge integrating techniques (e.g., such as image modalities that employ x-ray and/or gamma radiation). For example, medical, security, and/or industrial applications may utilize a computed tomography (CT) scanner comprising charge integrating channels that convert detected energy into signals (e.g., current or voltage signals) that are proportional to an incoming photon flux rate. The signals are processed by being integrated over a defined time period (e.g., at times referred to as a measurement interval), sampled, and digitized. Based upon the processed signals, one or more images providing a two-dimensional and/or three-dimensional representation of an object under examination may be generated therefrom.

BACKGROUND

Today, CT and other imaging modalities (e.g., single-photon emission computed tomography (SPECT), mammography, digital radiography, etc.) are useful to provide information, or images, of interior aspects of an object under examination. Generally, the object is exposed to radiation comprising photons (e.g., such as x-rays, gamma rays, etc.), and an image is formed based upon the radiation absorbed and/or attenuated by the interior aspects of the object, or rather an amount of photons that is able to pass through the object. Generally, highly dense aspects of the object absorb and/or attenuate more radiation than less dense aspects, and thus an aspect having a higher density, such as a bone or metal, for example, will be apparent when surrounded by less dense aspects, such as muscle or clothing.

Radiographic imaging modalities generally comprise, among other things, a detector array comprised of a plurality of channels that are respectively configured to convert radiation traversing the object into signals that may be processed to produce the image of the object. The channels are typically "charge integrating" and/or "photon counting" type channels (e.g., the imaging modality operates in charge integration mode, photon counting mode, or both).

Photon counting channels are configured to convert energy into signals that are proportional to the energy of a detected photon (e.g., at times referred to as a detection event). Thus, ideally, signals produced by respective channels generally comprise one or more current and/or voltage pulses, for example, respectively associated with a single detection event. A controller may then be used to determine the location and energy of respective detection events, accumulate the detection events occurring during a measurement interval (e.g., an "acquisition view"), digitize the information, and/or process the digital information to form an image, for example.

Photon counting channels have several advantages over charge integrating channels. The counting of photons is substantially noise free (e.g., apart from inherent photon shot noise). Therefore, a lower dose of radiation may be applied to the object under examination. Moreover, photon counting channels generally allow for energy or wavelength discrimination. Therefore, images resulting from radiation emitted at different energy levels may be obtained at the same or substantially the same time, for example.

Despite such advantages, photon counting detector arrays have not been widely adopted in some imaging modalities (e.g., such as CT) that have a high photon emission rate. One factor inhibiting widespread adoption is saturation issues (e.g., pulse pileup) for individual channels in photon counting detector arrays. Saturation occurs when photons are detected at a rate that causes one or more channels to be unable to return to a normal state after the detection of a photon before another photon is detected. For example, individual channels of the detector array are configured to emit an electric pulse when a photon is detected. The electric pulse is intended to be merely indicative of a single detection event and is typically counted as a single detection event. However, when two or more photons reach the same channel at approximately the same time, the emitted electric pulse may be indicative of two or more detection events. Because the affected channel was not able to return to an electrically normal state between the detection of second, third, etc. photons, the pulses emitted by the channel are said to "pile-up" into a single pulse, indicative of a single response to multiple received photons. Because the counters are typically configured to count a single detection event per pulse, the counters may mistakenly count merely a single detection event when the pulse is, in fact, indicative of two or more detection events. Thus, due to this phenomenon, photon counting detector arrays are generally unable to process photon emission rates normally utilized in computed tomography scanners and/or other imaging modalities.

Charge integrating channels, interchangeably referred to as "charge integration channels," have the potential to detect photons at a faster rate than photon counting detector channels, thereby at least partially mitigating the saturation issue. However, there is a lower limit of detection defined by noise in each charge integrating channel such that a channel with little to no incident radiation may produce some signal due to thermal and/or analog read noise (e.g., produced by the detector array and/or readout components). Some channels may be affected by the lower detection limit to a greater extent than other channels. For example, depending on the patient cross section and bowtie filter profile, some channels may detect few, if any photons, compared to the quantity of photons detected by other channels. Since the noise exhibited by each channel is similar, the signal-to-noise ratio ("SNR") for the channels detecting the relatively small quantity of photons is lower than the SNR for the other channels that detect the relatively large quantity of photons. The number of channels that exhibit a poor SNR increases inversely to the size of those channels (e.g., more channels are likely to exhibit a low SNR the smaller the channels are).

Further, charge integrating channels are separated from each other in the detector array by non-detecting borders referred to as septa. A detector array comprising small charge integrating channels (e.g., detecting surface areas of less than 1 $mm^2$) results in a substantial percentage of the detector array being formed from non-detecting regions. Since photons impinging on the non-detecting regions are not traditionally accounted for in the resulting images, small charge integrating detectors are believed to introduce significant noise into the images. Accordingly, conventional radiation imaging modalities have avoided the use of small charge integrating channels.

In an effort to mitigate the low-SNR and non-detecting-region issues, charge integrating channels can be made large (e.g., having a detection surface area of at least 1 $mm^2$) throughout the detector array. Large channels increase the surface area for detecting photons, thus increasing the likelihood that at least a minimal number of photons are received by each large channel. However, increasing the size of the channels in the detector array negatively affects the resolution and image quality of the images generated from the detected radiation. Further, proximate channels that are large can cause those channels to receive a quantity of photons that may be difficult to process. Thus, a detector array formed from large physical charge integrating channels is also associated with drawbacks.

BRIEF SUMMARY

Aspects of the present disclosure address the above matters, and others. According to one aspect a system for an imaging modality is provided. The system comprises a radiation source configured to emit radiation photons and a detector array configured to detect radiation photons emitted by the radiation source. The detector array includes a plurality of charge integrating channels that are configured to generate a signal. The system also includes a channel combining component configured to combine information generated by more than one of the plurality of charge integrating channels to generate one or more virtual channels. The information for the virtual channels represents a combination of information for at least two charge integrating channels.

According to another aspect, a method for generating virtual channels in an imaging modality is provided. The method includes generating information from respective charge integrating channels of a detector array, the generated information is indicative of x-ray energy detected by the charge integrating channels that is integrated over a defined time period for the respective charge integrating channels. The method also includes generating a first virtual channel representing two or more of the charge integrating channels based at least in part upon the generated information obtained using the respective two or more of the charge integrating channels.

According to yet another aspect, a computer-readable medium storing computer executable instructions that, when executed via a computer processing system, performs a method is provided. The method includes generating information for respective charge integrating channels of a detector array. The generated information is indicative of x-ray energy detected by the respective charge integrating channels that is integrated over a defined time period. The method also includes generating a first virtual channel representing two or more of the charge integrating channels based at least in part upon the generated information.

Those of ordinary skill in the art will appreciate still other aspects of the present disclosure upon reading and understanding the appended description.

BRIEF DESCRIPTION OF THE DRAWINGS

The present disclosure is illustrated by way of example and not limitation in the figures of the accompanying drawings, in which like references generally indicate similar elements and in which.

DETAILED DESCRIPTION

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

Among other things, one or more systems and/or techniques are provided herein for combining information from two or more charge integrating channels of a detector array to generate one or more virtual channels. The one or more virtual channels have an effective detection surface area that is typically larger than a detection surface area of the individual charge integrating channels used to detect the combined information. Stated differently, conventional detector arrays are comprised of channels having a detection surface area measuring at least 1 mm$^2$. A charge integrating detector array, as provided for herein, may comprise charge integrating type channels that respectively have a smaller detection surface than conventional channels (e.g., the individual channels may have a detection surface area measuring 0.5 mm$^2$ or less, or a detection surface area measuring 0.25 mm$^2$ or less, or a detection surface area measuring 0.2 mm$^2$ or less), for a given detector array size, that remains unchanged from the conventional detector array size. In other words, there may be more channels per unit area for a given detector array size, relative to a conventional detector array. Data (or signals) from a plurality of (e.g., two or more) channels may be combined to create a virtual channel (e.g., also referred to herein as a synthetic channel and/or the like) indicative of the output from the plurality of channels. In this way, it may be said that one or more physical channels are oversampled (e.g., the information from one or more physical channels is combined) to form an output (e.g., a virtual channel) indicative of the oversampling (e.g., or combination). In one embodiment, at least some of the virtual channels may respectively represent a portion of the detection surface substantially equivalent to the detection surface of a conventional channel (e.g., the virtual channel may represent a plurality of channels that, when combined, have a detection surface area of approximately 1 mm$^2$), although respective virtual channels may be larger or smaller than a conventional channel.

A higher resolution image can be generated based on the radiation detected by the relatively-small channels compared to conventional large channels.

It will be appreciated that there are many bases upon which data from charge integrating channels can be combined to create virtual channels in accordance with the provisions set forth herein, which may provide numerous benefits over conventional channels. In one embodiment, channels may be selected to be combined to form virtual channels in a manner that mimics a flying focal spot in the x and/or z direction for a same and/or similar acquisition view. By way of example, from one acquisition view (e.g., from data acquired during a single measurement interval), 4 or more views could be created depending, at least in part, upon the number of channels represented in the virtual channel(s). Respective views that are created may be offset by a specified amount in the x and/or z direction to mimic views acquired using a flying focal spot (e.g., without having to actually use a radiation source that comprises a flying focal spot).

In another embodiment, one or more virtual channels may have a detector surface that is smaller than a detector surface of a conventional channel, allowing higher resolution images to be generated relative to the resolution of conventional images. Such higher resolution images (e.g., which are typically noisy images) may be used in combination or conjunction with lower resolution images (e.g., which are typically less noisy than the higher resolution images), indicative of larger virtual channels, for iterative reconstruction. For example, edge information may be acquired from the higher resolution images and contrast information may be acquired from the lower resolution images.

Yet another benefit is that the virtual channels can be created in locations that are specified by a reconstruction algorithm (e.g., the effective location of (e.g., center of) the virtual channel can be located at a specified position) such that actions during reconstruction may be reduced (e.g., radial and/or z-interpolation acts may be eliminated). As another benefit, the detection area of respective virtual channels may be increased and/or decreased as a function of the measured dose (e.g., the radiation detected and integrated by the detector array), for example, to reduce noise that may be introduced by cells that detect little, if any radiation yet still generate a low-limit amount of noise, for example, during data acquisition. It will be appreciated that these and other benefits may be further realized from the following description.

Figure 1:
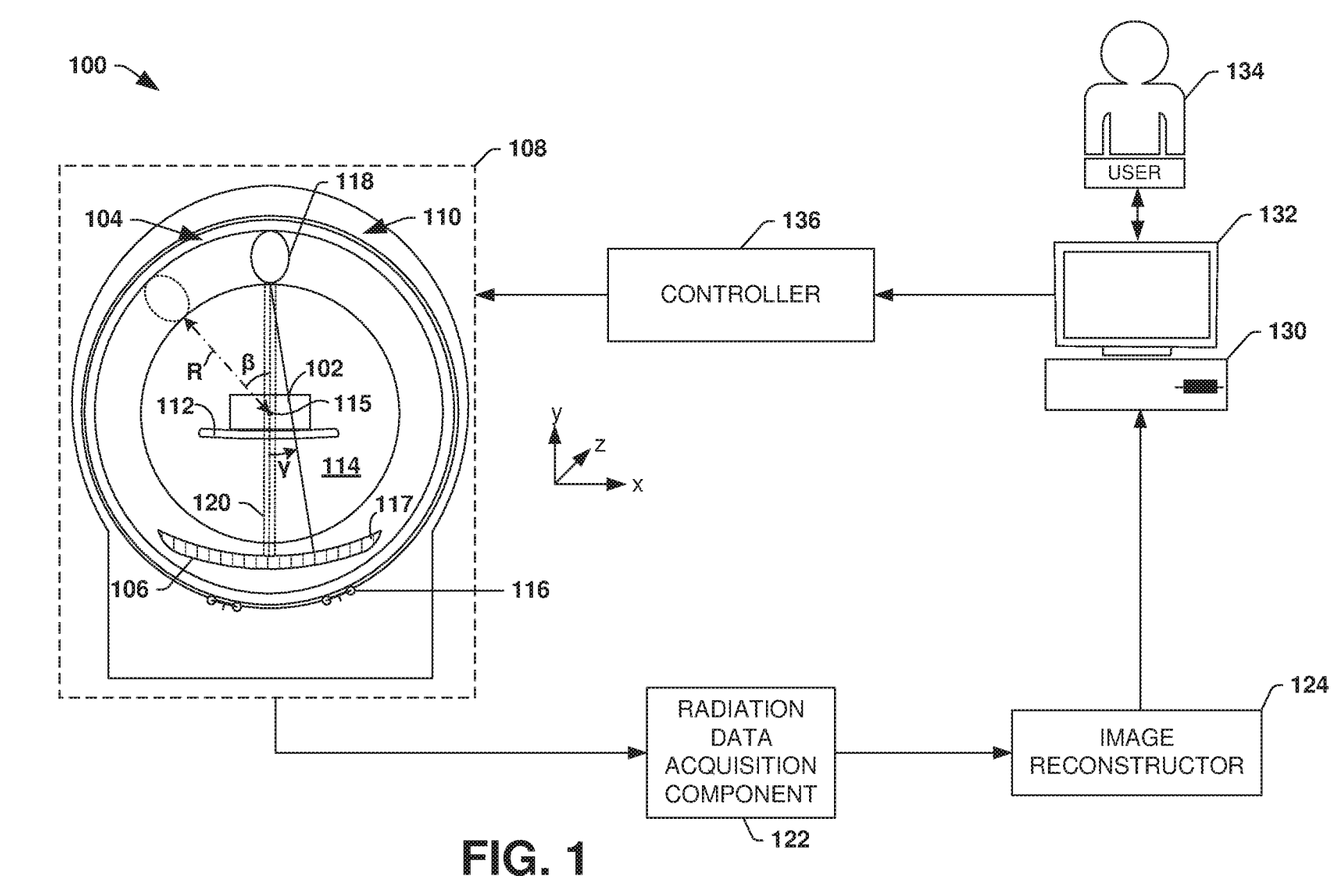
FIG. 1 is an illustrative embodiment of an environment of a first image modality configured to employ charge integrating technology.

With reference to the drawings, FIG. 1 is an illustration of an illustrative environment 100 comprising a computed tomography (CT) system that may be configured to generate computed tomography images representative of an anatomical object 102 (e.g., patient, organ, muscle, tissue, etc.) or aspect(s) thereof. Such a system is an example of a medical modality that may be employed to generate images of patient regions using charge integrating channels of a detector array 106. However, the methods and systems described herein are not limited to generating images of patients captured by medical modalities. Any image captured by charge integrating channels of a radiation detector array 106 can be the subject of the methods and systems described herein. Moreover, the placement of components is merely intended to be provided as an example and may not necessarily detail possible arrangements and/or configurations. For example, in one embodiment, the radiation data processor 122 may be coupled to a rotating gantry 104 of the imaging modality, or comprised within a detector array 106.

Further, it may be appreciated that while the environment 100 in FIG. 1 describes a CT system configured to generate two-dimensional and/or three-dimensional images of the object 102 under examination, other radiation imaging modalities are also contemplated for generating images of the object 102, optionally for diagnostics purposes. Further, the disclosure, including the scope of the claims, is not intended to be limited to a particular type(s) of imaging modality(ies) to the extent practical, but rather the systems and/or techniques described herein may be used in conjunction with a wide variety of imaging modalities, such as, but not limited to, SPECT, mammography, and/or digital radiography, etc., for example. For the sake of brevity and clarity, however, the example of an image of a patient region in the form of a CT scan is described herein for illustrative purposes.

In the embodiment of the environment 100 in FIG. 1, an examination apparatus 108 of the CT system is configured to examine one or more objects 102, including an anatomical object prone to movement, such as an organ of the patient. The examination apparatus 108 can comprise a rotating gantry 104 and a (stationary) support structure 110 (e.g., which may encase and/or surround at least a portion of the rotating gantry 104 (e.g., as illustrated with an outer, stationary ring, surrounding an outside edge of an inner, rotating ring)). During an examination of the object 102, the object 102 can be placed on a support article 112, such as a bed or conveyor belt, for example, that is selectively positioned in an examination region 114 (e.g., a hollow bore in the rotating gantry 104), and the rotating gantry 104 can be rotated and/or supported about an axis of rotation 115, and about the object 102 by a rotator 116, such as a motor, drive shaft, chain, roller truck, etc.

The axis of rotation 115 for a cylindrical CT system may be located at the center of the examination region 114, which is also the isocenter of the examination apparatus 108. The isocenter is the space through which the central ray of a set of radiation beams 120 passes, and the object 102 may be positioned within the examination region 114 so the region of interest (e.g., an organ of the patient to be shown in the image) is centered at, or located adjacent to the location of isocenter. The distance R from the radiation source(s) 118 to isocenter is represented in broken lines in FIG. 1.

The rotating gantry 104 may surround a portion of the examination region 114 and may comprise one or more radiation sources 118 (e.g., an ionizing x-ray source, gamma radiation source, etc.) and a detector array 106 that is mounted on a substantially diametrically opposite side of the rotating gantry 104 relative to the radiation source(s) 118. The rotating gantry 104 can be rotated to sweep the radiation source(s) 118 through the plurality of angular locations about the axis, making full 360° revolutions. The angle β in FIG. 1 generally represents the gantry angle or the source angle at the different angular locations of the views as described below. During an examination of the object 102, the radiation source(s) 118 emits fan, cone, wedge, parallel beam (shown in the drawings), and/or other shaped radiation 120 configurations from a focal spot(s) of the radiation source(s) 118 (e.g., a region within the radiation source(s) 118 from which radiation 120 emanates) into the examination region 114. Such radiation 120 may be emitted substantially continuously and/or may be emitted intermittently (e.g., a brief pulse of radiation is emitted followed by a resting period during which the radiation source(s) 118 is not activated).

As the emitted radiation 120 traverses the object 102, the radiation 120 may be attenuated differently by different aspects of the object 102. Because different aspects attenuate different percentages of the radiation 120, one or more image(s) may be generated based upon the attenuation, or variations in the number of photons that are detected by the detector array 106. For example, more dense aspects of the object 102, such as a bone, a metal plate, electronic components, etc., may attenuate more of the radiation 120 (e.g., causing fewer photons to strike the detector array 106) than less dense aspects, such as skin or clothing.

The detector array 106 is configured to directly convert (e.g., using amorphous selenium and/or other direct conversion materials) and/or indirectly convert (e.g., using photodetectors and/or other indirect conversion materials) detected radiation into signals that can be transmitted from the detector array 106 to the radiation data processor 122 configured to compile signals that were transmitted within a predetermined time interval, or measurement interval, using various techniques. For example, the detector array 106 can convert x-ray energy received by the individual channels into current signals that are integrated over a time period, then measured and ultimately digitized. It may be appreciated that such a measurement interval may be referred to as a "view" and generally reflects signals generated from radiation 120 that was emitted while the radiation source(s) 118 was at a particular angular location relative to the object 102. Based upon the compiled signals, the radiation data processor 122 can generate projection data indicative of the compiled signals, for example.

Figure 2:
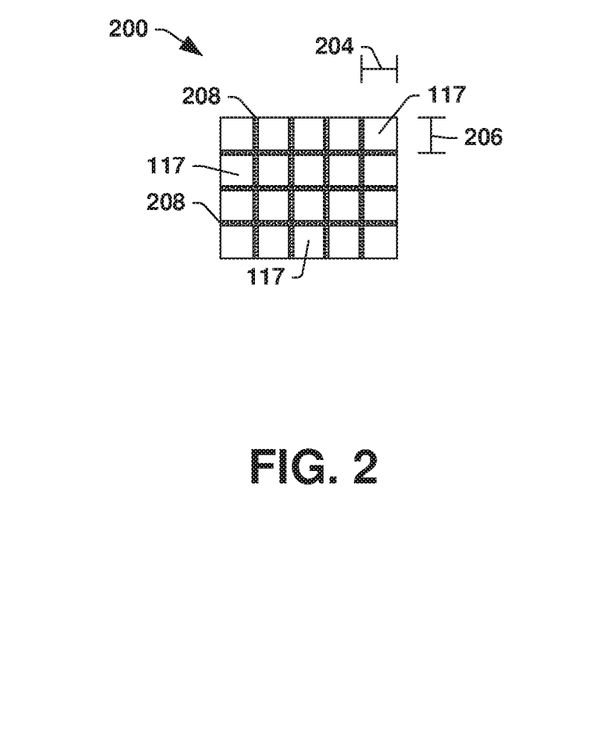
FIG. 2 illustrates an embodiment of an indirect conversion, charge integrating detector array.

The detector array 106 may be divided into a plurality of individual charge integrating channels 117, interchangeably referred to herein as channels 117, arranged in rows and columns, as shown schematically in FIG. 2. Using the XYZ coordinates of FIG. 1 as a reference, the channels 117 may be arranged in rows that extend in the X direction, and columns that extend in the Z direction, which is a direction parallel with the axis of rotation 115. The fan angles γ in FIG. 1 are the individual angle of each channels 117, as seen from the radiation source(s) 118, or the angle relative to the center ray emitted by the radiation source(s) 118.

The detector array 106 is generally operated in a charge integration mode (e.g., as opposed to a photon counting mode). That is, the channels 117 are of a charge integrating type and are configured convert energy (e.g., in the case of CT scanners, x-ray energy) into current signals that are integrated over a defined time period, then measured and ultimately digitized. Thus, signals produced by respective channels generally comprise one or more current and/or voltage pulses, for example, respectively associated with the quantity of x-ray energy received at the surface of the individual channels 117. For example, an embodiment of the CT system using forty (40 mm) millimeter (or four (4 cm) centimeter) collimation includes sixty four (64) rows of channels 117 to capture each of four slices that are to be assembled into a single three-dimensional image encompassing a portion of the object 102. A set of parallel x-ray beams, referred to herein as parallel rays 120, emitted by the radiation source(s) 118 encounter the object 102 before being received by the channels 117.

Signals that are produced by the detector array 106, or rather by the channels 117 of the detector array 106, may be transmitted to the radiation data processor 122 in operable communication with the detector array 106. The radiation data processor 122 (e.g., which may be referred to as a controller) is configured to receive the signals and generate charge integration data indicative of, among other things, a location and detection time for respective photons detected by the channels 117 of the detector array 106.

The detection times of respective photons may respectively correlate to a particular known position of the radiation source(s) 118 at those detection times. It will be appreciated that in some instances (e.g., because of practical limitations of the radiation data processor 122), the radiation data processor 122 may bin data related to the charge integrations into temporal acquisition bins based upon their respective detection times. For example, the radiation data processor 122 may be unable to correlate the radiation signals integrated with a position of the radiation source(s) 118 at the instance the radiation is detected by the detector array 106, so the radiation data processor 122 may bin the photons that were detected in a particular time interval together and determine an approximate position of the radiation source 118 during that interval of time (e.g., which may be referred to as an acquisition view and/or the like). It will be understood that the number of temporal acquisition bins, which respectively correspond to an acquisition view, should be relatively large to reduce tangential blurring (e.g., caused when respective bins represent photons emitted during a larger span along the trajectory or movement of the radiation source(s) 118).

Moreover, as will be described in more detail below, in one embodiment, the radiation data processor 122 may create virtual channels based upon the data yielded from respective channels of the detector array 106. For example, the data yielded from two or more channels of the detector array 106 may be combined to represent a single virtual channel that has a detection surface area greater in size than the detection surface area of any one of the two or more channels 117 individually (e.g., the single virtual channel may have a detection surface area substantially equivalent to the detection surface area of the two or more channels 117 that are combined to form the virtual channel). Additional features of the radiation data processor 122 may be described below, but, in one embodiment, comprises weighting the contribution of respective channels to a virtual channel such that the integration result associated with a virtual channel is substantially equivalent to an average of the integration result for the individual channels 117 that are represented by the virtual channel.

The example environment 100 also illustrates as image reconstructor 124 that is operably coupled to the radiation data processor 122 and is configured to generate one or more images representative of the object 102 under examination using suitable analytical, iterative, and/or other reconstruction technique (e.g., tomosynthesis reconstruction, back-projection, etc.). Generally, respective images focus on a plane (e.g., or slice) of the object 102 under examination.

The illustrative environment 100 further comprises a terminal 130, or workstation such as a computing device 312, described below with reference to FIG. 3, that may be configured to receive the image data captured by the examination apparatus 108. The terminal 130 may also be configured to present the image data and/or information for display on a monitor 132 to a user 134 (e.g., medical personnel, etc.). In this way, the user 134 can inspect the image(s) to identify areas of interest within the object 102, possibly for diagnostic purposes. The terminal 130 can also be configured to receive user input, which can direct operations of the examination apparatus 108 (e.g., a speed of a conveyor belt), for example.

Figure 3:
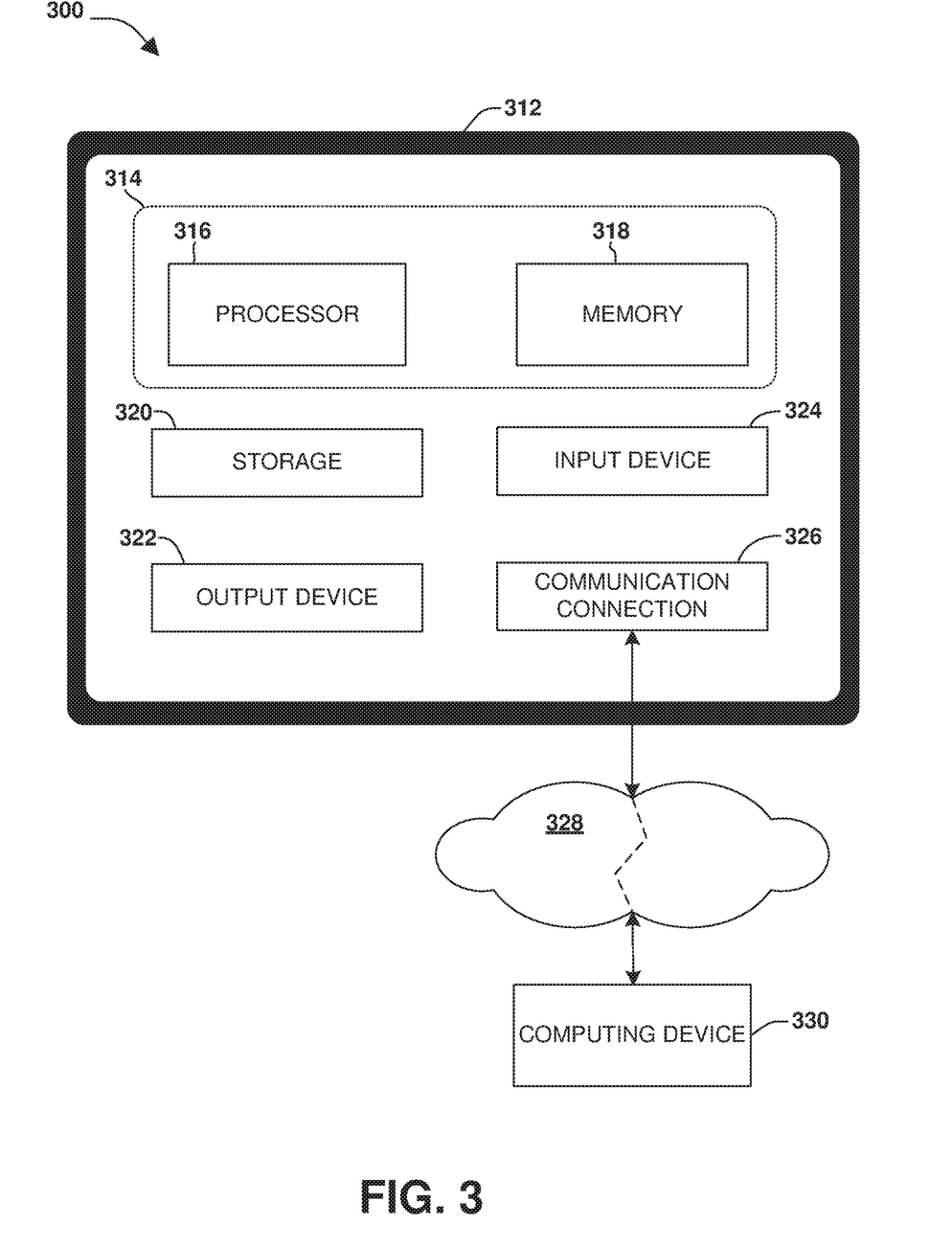
FIG. 3 illustrates an example of a computing device.

FIG. 3 illustrates an example of a system 300 comprising a computing device 312 configured to implement one or more embodiments provided herein. In one configuration, the computing device 312 includes at least one processor 316 and memory 318. Depending on the exact configuration and type of computing device, memory 318 may be volatile (such as RAM, for example), non-volatile (such as ROM, flash memory, etc., for example) or some combination of the two. This configuration is illustrated in FIG. 3 by dashed line 314.

Figure 6:
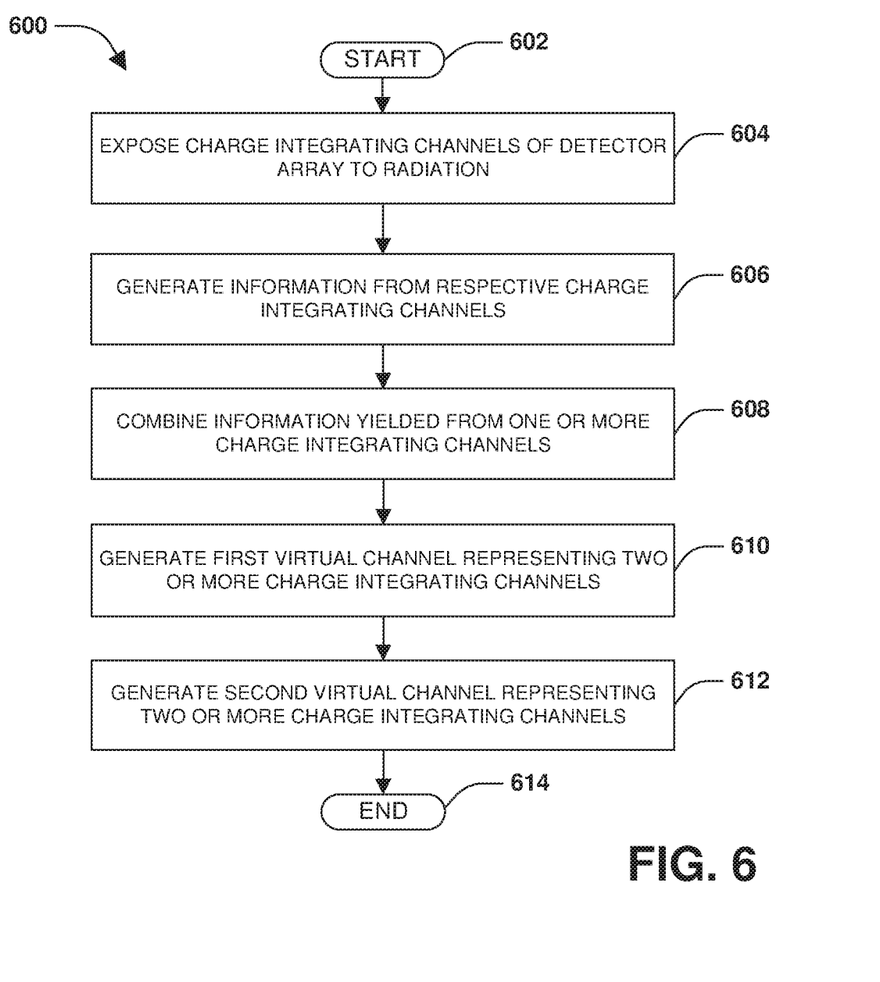
FIG. 6 is an example flow diagram illustrating an example method for generating virtual channels in an imaging modality.

In other embodiments, the computing device 312 may include additional features and/or functionality. For example, the computing device 312 may also include additional storage (e.g., removable and/or non-removable) including, but not limited to, magnetic storage, optical storage, and the like. Such additional storage is illustrated in FIG. 6 by storage 320. In one embodiment, computer-readable instructions to implement one or more embodiments provided herein may be in storage 320. Storage 320 may also store other computer-readable instructions to implement an operating system, an application program, and the like. Computer-readable instructions may be loaded in memory 318 for execution by processor 316, for example. The computing device 312 may include an input device 324 and an output device 322.

The term "computer-readable media" as used herein includes computer storage media. Computer storage media includes volatile and nonvolatile, removable and non-removable media implemented in any method or technology for storage of information such as computer-readable instructions or other data. Memory 318 and storage 320 are examples of computer storage media. Computer storage media includes, but is not limited to, RAM, ROM, EEPROM, flash memory or other memory technology, CD-ROM, Digital Versatile Disks (DVDs) or other optical storage, magnetic cassettes, magnetic tape, magnetic disk storage or other magnetic storage devices, or any other medium that can be used to store the desired information and can be accessed by the computing device 312. Computer storage media does not, however, include propagated signals. Rather, computer storage media excludes propagated signals. Any such computer storage media may be part of computing device 312.

Computing device 312 may also include communication connection 326 that allows the computing device 312 to communicate with other computing devices 330 over a local and/or wide area network 328. Communication connection 326 may include, but is not limited to, a modem, a Network Interface Card (NIC), an integrated network interface, a radio frequency transmitter/receiver, an infrared port, a USB connection, or other interfaces for connecting computing device 312 to other computing devices 330. Communication connection 326 may include a wired connection or a wireless connection. Communication connection 326 may transmit and/or receive communication media.

In the illustrated embodiment environment 100, a controller 136 is operably coupled to the terminal 130. In one example, the controller 136 is configured to receive input from the terminal 130, such as user input for example, and to generate instructions for the examination apparatus 108 indicative of operations to be performed. For example, the user 134 may desire to reexamine the object 102, and the controller 136 may issue a command instructing the support article 112 to reverse direction (e.g., bringing the object 102 back into an examination region 114 of the examination apparatus 108).

The component diagram of FIG. 1 is merely intended to illustrate one embodiment of one type of imaging modality and is not intended to be interpreted in a limiting manner. For example, the functions of one or more components described herein may be separated into a plurality of components and/or the functions of two or more components described herein may be consolidated into merely a single component. Moreover, the imaging modality may comprise additional components configured to perform additional features, functions, etc. and/or some components described herein may be optional.

FIG. 2 represents a portion 200 of the detector array 106 comprising indirect conversion, charge integrating channels 117, for detecting photons emitted at a high rate. Generally, respective channels 117 comprise a detection surface that faces the radiation source. The detection surface of each channel 117 can optionally have a surface area that is less than 1 $mm^2$, with borders extending in the x-dimension 204 and the z-dimension 206 measuring up to 1 mm or less in length. Channels 117 having such dimensions or surface areas have not previously been utilized because of a loss in detection efficiency. Detection efficiency is the number of photons detected when no object is being examined relative to the number of photons emitted when no object is being examined. Optical cross-talk also stood in the way of utilizing such small channels 117. Optical cross-talk between channels is a result of light emitted from the indirect conversion material being transferred from one channel to another channel. Moreover, non-detecting regions 208 (e.g., comprised of septa that mitigate a transfer of light from one channel to another) generally separate respective charge integrating channels 117 causing some of the radiation that impinges the detector array 106 to go undetected.

Figure 4:
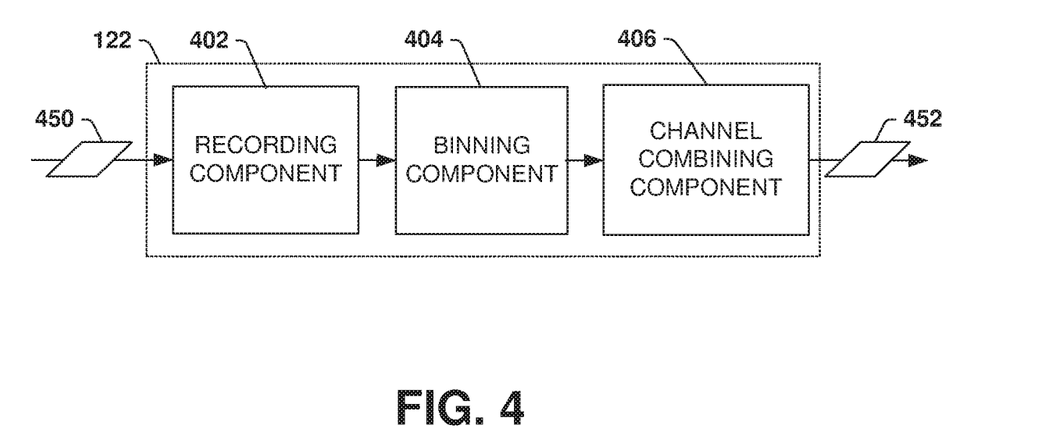
FIG. 4 illustrates an example radiation data processor configured to process signals generated by respective channels of a charge integrating detector array and combine information from two or more charge integrating channels to generate a virtual channel representing the two or more charge integrating channels.

FIG. 4 illustrates an illustrative embodiment of the radiation data processor 122 (FIG. 1) that is configured to receive signals 450 generated by individual charge integrating channels 117 (FIG. 1) and generate radiation data. The radiation data generated is indicative of, among other things, a location, detection time and measured charge of photons detected by the channels 117 of the detector array 106 (FIG. 1). Moreover, as will be described in more detail below, the radiation data processor 122 may be configured to generate virtual channels 502 and 504 and/or synthetic bins that may be transmitted to the image reconstructor 124 (FIG. 1) for image reconstruction.

As illustrated, the embodiment of the radiation data processor 122 comprises a recording component 402, a binning component 404, and a channel combining component 406. The recording component 402 is configured to record, among other things, a location, detection time and measured charge for the radiation samples detected by the individual channels 117 of the detector array 106, effectively causing each channel measurement to be recorded. As one example, the recording component 402 may comprise one or more comparators configured to compare the voltage and/or current of the signals 450 respectively output by the channels 117 to a signal comprising a baseline voltage/current. The comparison result can be correlated to a measured charge value, and the recording component 402 may record the measured charge in a relationship with a time when the charge was measured by the respective channel 117, and/or an identity of the channel 117 that emitted the signal 450 (e.g., a location within the detector array 106). It will be appreciated that in another embodiment, the recording component 402 may also record other information represented by the signal, such as, for example, an energy level or energy spectrum of detected radiation.

The binning component 404 is configured to, among other things, bin at least a portion of the data detected by the channels 117 during a given period of time into respective temporal acquisition bins representative of, among other things, the charge or other quality of radiation detected during a specified period of time and/or a location of a radiation source 118 (e.g., location of radiation source 118 at a time when radiation is measured). For example, given the number of channels 117 a detector array 106 may comprise and given that computation resources are finite, it may be a burden to determine a precise location of the radiation source 118 when the radiation was emitted. The binning component 404 may thus bin information regarding radiation detected by a channel 117 during a specified measurement interval (e.g., acquisition view) into a particular temporal acquisition bin. Respective temporal acquisition bins may therefore comprise information related to detected photons or other forms of radiation emitted from the radiation source 118 when the radiation source 118 was in a particular region (e.g., if the radiation source 118 is rotating and/or otherwise moving relative to an object 102 under examination). In this way, an approximate emission location or an approximate location (e.g., range of locations) of a radiation source 118 from which detected radiation was emitted may be determined, for example.

Moreover, in one embodiment (e.g., where an imaging modality is a multi-energy apparatus), the information may be further divided into temporal acquisition bins according to the energy level of respective detection events. For example, the binning component 404 may bin information indicative of higher energy radiation into a first set of temporal acquisition bins and may bin information indicative of lower energy radiation into a second set of temporal acquisition bins. Thus, the binning component 404 may divide acquired information from respective channels based upon, among other things, the time and energy level of detected radiation to which the information pertains.

The illustrated embodiment of the radiation data processor 122 further comprises a channel combining component 406 (FIG. 4) configured to combine information derived from signals generated by two or more of the plurality of charge integrating channels 117 to create a virtual channel representing a spatial region occupied by the two or more channels 117 on the detector array 106. In this way, the output 452 of the channel combining component 406 may be indicative of a virtual channel representing a larger area of the detection surface than the area occupied by any one of the channels whose information was combined to form the output. The output 452 of the channel combining component 406 (e.g., the virtual channels or synthetic bins representative of the virtual channels) may be output to an image reconstructor (e.g., 124 in FIG. 1), for example. For example, the channel combining component 406 can combine information derived from signals generated by at least N channels, where N can be any positive integer of at least 2, at least 3, at least 4, at least 5, at least 6, at least 7, at least 8, at least 9, or at least 10. According to other embodiments, N can be any positive integer greater than 10.

As an example, the channel combining component 406 may form a synthetic bin and create a virtual channel by combining a temporal acquisition bin indicative of information yielded from a first channel with a temporal acquisition bin indicative of information yielded from a second channel during a same or similar acquisition view. In this way, a virtual channel (e.g., representing an area of the detection surface that corresponds to an area occupied by the first and second channels) may be indicative of the radiation detected by the region represented by the virtual channel during the acquisition view.

In one embodiment, the act of combined information yielded from two more charge integrating channels 117 also comprises weighting information from the channels that are combined to form one or more virtual channel(s). As will be described in more detail below, the value a virtual channel is treated as having detected may be substantially an average of the value produced by integrating the data detected by the charge integrating channels 117 represented by the virtual channel (e.g., as opposed to a mere summation of the values). For example, where a virtual channel encompasses a region of the detector array 106 comprising 100 channels 117 that each have a detected value of 80 during an acquisition view, the virtual channel may merely be regarded as have an average value of 80, as opposed to 80,000 photons. It may be appreciated that this can normalize virtual channels relative to other channels 117 and/or relative to other virtual channels in applications where different virtual channels (e.g., representing a same acquisition view) comprise different numbers of channels 117 and/or where virtual channels are used in conjunction with mere channels 117. That is, the contribution of the virtual channel to resultant imagery is the same or substantially the same as that of other channels 117 and/or other virtual channels.

It may be appreciated that by weighting, the contribution of respective channels 117 of a first virtual channel may be weighted differently than the contribution of respective channels 117 of a second virtual channel. As an example, where the first virtual channel comprises 100 channels 117 and the second virtual channel merely comprises 10 channels 117, respective channels 117 of the first virtual channel may be weighted by a factor of 0.01 or 1/100 (1/n, where "n" is the number of channels 117 comprised in a virtual channel), whereas respective channels 117 of the second virtual channel may be weighted by a factor of 0.1 or 1/10.

It will also be appreciated that the number of charge integrating channels 117 represented by or comprised within a virtual channel and/or the weights applied to respective channels 117 may vary, for example, between applications, between acquisition views, and/or even within a same acquisition view. For example, the number of channels 117 represented by a virtual channel may be a function of, among other things, at least one of a location of a virtual channel relative to a center of the detector array 106, an amount of radiation emitted by the radiation source 118, an acquisition view that is being represented by the virtual channel, and/or an energy level of radiation detected by respective channels 117. By way of example, in one embodiment (e.g., where the number of channels 117 represented in a virtual channel is a function of a location of a virtual channel relative to a center of the detector array 106) (e.g., as further described with respect to FIG. 5), a first virtual channel on an outside edge of the detector array 106 may represent a larger portion of the detection surface than a second virtual channel approximate a center of the detector array 106 (e.g., to provide increase image resolution near a center of the image). As such, the first virtual channel may be comprised of information yielded from 200 channels 117 whereas the second virtual channel may be comprised of information yielded from 100 channels 117. Therefore, the information yielded from the 200 channels 117 that are represented by the first virtual channel may be weighted by 1/200th whereas the information yielded from the 100 channels 117 that are represented by the second virtual channel may be weighted by $1/100^{th}$.

As another example, the size of the virtual channels (e.g., an amount of detection surface that the virtual channels respectively represent) may be (automatically/programmatically or manually) increased and/or decreased based upon a dose applied by the radiation source 118 (e.g., the rate of photon emission and/or voltage applied to the radiation source 118) and/or based upon the radiation detected by respective charge integrating channels and/or by the detector array 106 as a whole, for example. By way of example, when the radiation source 118 is emitting photons at a higher rate, the size of respective virtual channels may be reduced (e.g., such that respective virtual channels represent fewer channels 117) relative to their size when photons are being emitted at a lower rate. Similarly, when a portion of the detector array 106 is starved of photons (e.g., because a portion of the object 102 being examined blocked a large percentage of the photons), the size of the virtual channel may be increased, relative to a default/specified size (e.g., to reduce the effect of photon starvation). Similarly, if an abundance of radiation is being detected by a region of the detector array 106, virtual channels representing that particular region of the detector array 106 may be reduced in size (e.g., such that respective virtual channels represent fewer channels 117 than a default/specified number) such that the radiation level detected per virtual channel is reduced (e.g., although the total number of virtual channels in the region may be increased to accommodate the reduced size of respective virtual channels). In this way, the size of respective virtual channels may be dynamically modified (e.g., on the fly) as a function of the rate at which radiation is being emitted and/or as a function of the quantity of radiation detected by respective channels 117, for example.

It will be appreciated that the instant disclosure, including the appended claims, contemplate any of a number of ways in which information from respective charge integrating channels 117 may be combined and/or weighted to create virtual channels, and information from respective charge integrating channels 117 may be combined/weighted in different ways depending upon the application. For example, in one embodiment, the information from channels 117 may be combined/weighted in a way that causes the data to mimic data produced by a flying focal spot in the x- and/or z-dimensions (e.g., where a focal spot from which radiation is emitted is moved relative to the detector array 106). This and/or other examples may be described in more detail below.

Virtual channels can represent equal numbers of charge integrating channels 117 in the x- and z-dimensions. According to other embodiments, however, one or more virtual channels may have a different (e.g., not square) shape, such as rectangular, trapezoidal, or other shape, for example (e.g., where the virtual channel represents a different number of charge integrating channels in the x-dimension than in the z-dimension). Moreover, it will be appreciated that, some of the virtual channels may represent a different number of charge integrating channels 117 than other virtual channels (e.g., even when representing a same acquisition view). Further, some virtual channels may spatially overlap other virtual channels (even when representing a same acquisition view).

Spatially overlapping virtual channels using the same and/or similar acquisition view data mimics a result of a focal spot shift in the data (e.g., without actually shifting the focal spot in the x- and/or z-dimensions via a flying focal spot technique). Because the virtual channels respectively represent a plurality of charge integrating channels, the channel combining component 406 (FIG. 4), for example, may be configured to generate two or more sets of virtual channels using data representative of a same/similar acquisition view. In such an embodiment, a second set of virtual channels may be offset from the first set of channels by a specified number of charge integrating channels 117. In such an example, two or more virtual channels, representing a same/similar acquisition view, may have one or more channels 117 in common (e.g., where a channel 117 is represented by or comprised within a first virtual channel in a first set of virtual channels and also comprised within a second virtual channel in a second set of virtual channels, where the second set of virtual channels is offset from the first set of virtual channels by a specified number of charge integrating channels 117).

It will also be appreciated that manipulating the location of virtual channels may be used for other purposes (e.g., and provide other benefits) besides mimicking a focal spot shift. For example, the channel combining component 406 may manipulate the effective channel position of a virtual channel(s) to reduce computational cost during image reconstruction. By way of example, the effective position of a virtual channel, for purposes of image reconstruction, is generally defined as a center measurement of the channel. Thus, by shifting the virtual channels, an effective position of the virtual channel is changed. It will be appreciated that the effective position of a virtual channel may also be changed by increasing or decreasing the number of channels 117 that are represented by a virtual channel. Furthermore, by adjusting the weights used in combining the charge integrating channels 117 into virtual channels, one can achieve almost any desired center location for resulting virtual channels.

Further, as described above, the number of channels 117 represented by respective virtual channels may differ between imaging modality applications, between acquisition views, and/or even within a same acquisition view, for example. In this way, in some embodiments, one or more virtual channels may represent a larger portion of the detection surface than other virtual channels.

Figure 5:
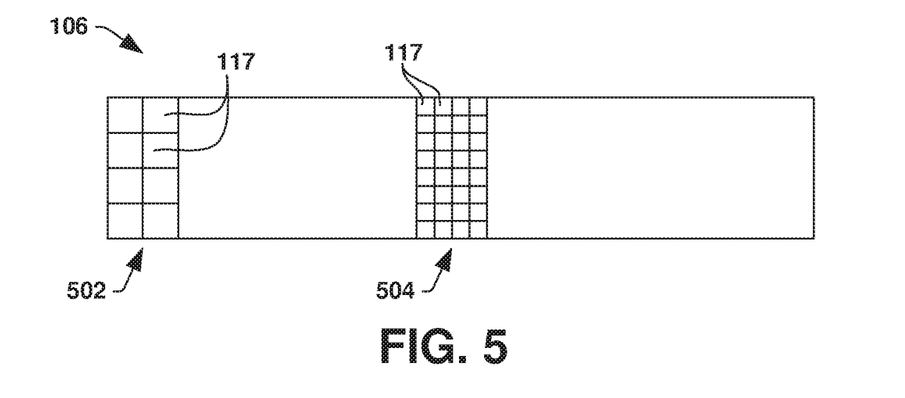
FIG. 5 illustrates a top-down view of an example charge integrating detector array wherein virtual channels of varying sizes are imposed.

FIG. 5 is a top-down view of an illustrative embodiment of the detector array 106 (FIG. 1), where virtual channels 502, 504, encompassing charge integrating channels 117 counted during a single acquisition view, are imposed upon portions of the detector array 106. It will be appreciated that, although not illustrated, the example detector array 106 may comprise additional charge integrating channels 117 and/or additional virtual channels. FIG. 5 merely provides example sets of virtual channels 502, 504 to illustrate how some virtual channels may differ in size relative to other virtual channels, even within a same acquisition view. As illustrated, a first set of virtual channels 502 representing or comprising charge integrating channels near an edge portion of the detector array 106 (which may be relatively far apart from isocenter in the present example) respectively represent a larger portion of the detection surface than a second set of virtual channels 504 representing or comprising charge integrating channels 117 closer to a center portion of the detector array 106 (which may be relatively close to isocenter in the present example).

In one embodiment, it is preferable that the detection surface of respective charge integrating channels 117 is substantially uniform (e.g., respective channels comprise an area of up to approximately 0.25 mm$^2$). As a result, in such an embodiment, the number of channels 117 represented by respective virtual channels may be varied (e.g., by a channel combining component (e.g., 406 in FIG. 4)) to vary the size of respective virtual channels. For example, respective virtual channels of the first set of virtual channels 502 may represent or comprise 200 charge integrating channels 117, whereas merely 100 charge integrating channels 117 may be represented by or comprised within respective virtual channels of the second set of virtual channels 504. Thus, within a same acquisition view, a first virtual channel (e.g., comprised in the first set of virtual channels 502) may represent a different number of charge integrating channels 117 than a second virtual channel (e.g., comprised in the second set of virtual channels 504).

FIG. 6 illustrates an illustrative method 600 for generating virtual channels in an imaging modality. Such a method 600 may find applicability with respect to radiographic imaging modalities that generate images based upon radiation. More particularly, the example method 600 finds applicability with respect to imaging modalities that comprise a charge integrating detector array 106 comprised of a plurality of charge integrating channels 117. As an example, the method 600 may be used in CT applications where x-ray energy detected by the channels 117 is converted into current signals that are integrated over a finite time period, then measured and digitized and transmitted for image reconstruction.

The illustrative method 600 begins at 602 and charge integrating channels 117 of a detector array 106 are exposed to radiation at 604. The radiation may be x-rays, gamma-rays, and/or other forms of radiation that comprise photons and that may be used for imaging an object 102 under examination. Moreover, the channels 117 may be exposed to radiation within a single energy spectrum and/or within two or more energy spectra.

At 606 in the example method 600, information is generated from respective charge integrating channels 117 as a result of the detection of radiation. The information is generally indicative of a charge of radiation detected by the channels 117 during an acquisition view, but can be indicative of any other quantity such as an energy level/spectrum of detected radiation, a location along a gantry from which the detected radiation was respectively emitted, etc.

While already described in detail above, it will be appreciated that the charge integrating channels 117 are typically indirect conversion channels respectively occupying a portion of the detection surface that is generally smaller than conventional charge integrating channels (e.g., less than 1 mm$^2$). The channels 117 are also typically uniform across the detector array 106, although in one embodiment, some of the channels 117 may occupy a larger portion of the detector surface than other channels (e.g., and some channels may be larger than 1 mm$^2$).

At 608 in the example method 600, information yielded from one or more charge integrating channels 117 is combined, and virtual channels may be yielded therefrom. For example, at 610 in the example method 600, a first virtual channel representing two or more channels 117 is generated and at 612 in the example method, a second virtual channel representing two or more channels 117 is generated. Generally, the first virtual channel and the second virtual channel represent different charge integrating channels, although there may be some overlap (e.g., causing the first virtual channel to spatially overlap the second virtual channel).

Generally, combining the information yielded from one or more channels 117 causes a virtual channel to be created that is greater in area than that of a single one of the channel 117. Stated differently, the output (e.g., the virtual channel) may represent a larger portion of the detection surface (e.g., 1 mm$^2$) than the individual charge integrating channels 117 whose information is combined for the virtual channel (e.g., which may each merely represent 0.25 mm$^2$ of the detection surface).

It will be appreciated that in one embodiment, combining the information yielded from two or more charge integrating channels 117 may involve more than, or different than a mere summation of the information. For example, some virtual channels may be larger in size and/or represent a greater number of charge integrating channels 117 than other virtual channels (e.g., even representing a same acquisition view). For example, a first virtual channel may be formed by combining information from merely 2 charge integrating channels 117 while a second virtual channel may be formed by combining information from 10 or more charge integrating channels 117. For example, the number of channels 117 represented by a virtual channel may be a function of at least one of a location of a virtual channel relative to a center of the detector array 106, an amount of radiation emitted by the radiation source 118, an acquisition view that is being represented by the virtual channel, and/or a quantity or quality of radiation detected by respective channels 117, among other things.

Because charge integrating channels 117 may be combined differently (e.g., virtual channels may represent a different number of charge integrating channels 117), a mere summation of the information may result in a first virtual channel (e.g., representative of ten channels 117) having a different gain relative to a second virtual channel (e.g., representative of merely two channels 117). As mentioned above, weighting may be implemented whereby the sum total of respective channels 117 of a particular virtual channel may be divided by the number of channels 117 of the particular virtual channel and/or a weight (e.g., indicative of a contribution that a channel 117 makes to the virtual channel) may be applied.

It will be appreciated that while reference is made herein to weighting respective charge integrating channels 117, or information yielded from the respective channels 117, even when represented by a same virtual channel (e.g., such that each of 100 channels 117 have a 1% contribution to the virtual channel), some channels 117 that contribute to a same virtual channel may be weighted differently than other channels. By way of example, suppose a charge integrating channel 117 comprised a manufacturing defect that caused the charge integrating channel 117 to detect a lower than desired (e.g., lower than average) quantity of radiation. A different weight may be applied to the defective charge integrating channel, relative to the weight applied to other charge integrating channels 117 (e.g., or information yielded therefrom), to account for the manufacturing defect.

As described above, there are numerous factors that may play a role in determining how to combine information from one or more charge integrating channels 117 of the detector array 106 to generate one or more virtual channels, and the factors that are taken into consideration may depend upon the application to which the example method 600 is applied. For example, in one embodiment, a plurality of different virtual channel sets are created from the same acquisition view, with virtual channels in a second set being offset by a predetermined number of charge integrating channels 117 relative to virtual channels in a first set (e.g., to mimic a flying focal spot). In this way, two or more virtual channels that at least partially overlap in the spatial domain (e.g., represent or comprise one or more of the same channels 117) may be generated. Moreover, in another embodiment, the effective position (e.g., location) of one or more virtual channels may be adjusted based upon image reconstruction considerations. The effective position of a virtual channel (e.g., or of any channel for that matter) is generally considered to be a center point of the virtual channel and calculations may be made with respect to the channel and/or virtual channel (e.g., by an image reconstructor 124) based upon the determined effective position of the virtual channel and/or channel. Therefore, by adjusting a number of charge integrating channels 117 that are combined to create a virtual channel and/or adjusting which charge integrating channels 117 are combined to create a virtual channel, and/or adjusting the weights applied to individual charge integrating channels 117 in the process of combining them, the effective position of the virtual channel can be adjusted in a manner that causes the virtual channel to be located in a desired position (e.g., that reduces and/or eliminates operations (e.g., interpolations) performed during image reconstruction).

Another factor that may be considered is image resolution, which may be altered by adjusting how charge integrating channels 117 (or information derived therefrom) is combined (e.g., to cause the virtual channels to increase or decrease in size). Generally speaking, the larger a virtual channel, the lower the resolution because a larger virtual channel represents or 'consumes' a larger surface area of the detector array 106 than smaller virtual channels and/or charge integrating channels. The larger surface area can be analogized to generating a computer-generated image from larger pixels instead of using smaller pixels corresponding to the smaller virtual channel. That is, a configuration where 100,000 charge integrating channels 117 of a detector array 106 are arranged into 5000 virtual channels may yield a higher resolution image than a configuration where the 100,000 charge integrating channels 117 are arranged into 1000 virtual channels because the detector array effectively comprises five times as many channels in the 5000 virtual channel configuration than in the 1000 virtual channel configuration (e.g., each virtual channel of the 1000 virtual channel arrangement occupies or 'consumes' five times more charge integrating channels than each virtual channel of the 5000 virtual channel arrangement). As a corollary, generally speaking, higher resolution images may also be more noisy than lower image resolutions because respective virtual channels represent fewer charge integrating channels (e.g., the total detected radiation represented by a virtual channel is less because fewer charge integrating channels are represented by the virtual channel). Thus, the size of the virtual channels may be altered according to whether it is desirable to produce high resolution images or to produce less noisy images. For example, high resolution images may be desired for edge detection, whereas less noisy images may be desirable for contrast images. Therefore, in one embodiment, two sets of virtual channels may be created from an acquisition view. The first set may comprise (an increased number of) smaller virtual channels to produce high resolution images for edge detection and the second set may comprise (a lesser number of) larger virtual channels to produce lower resolution, less noisy images for contrast images, for example.

The example method 600 ends at 614.

Figure 7:
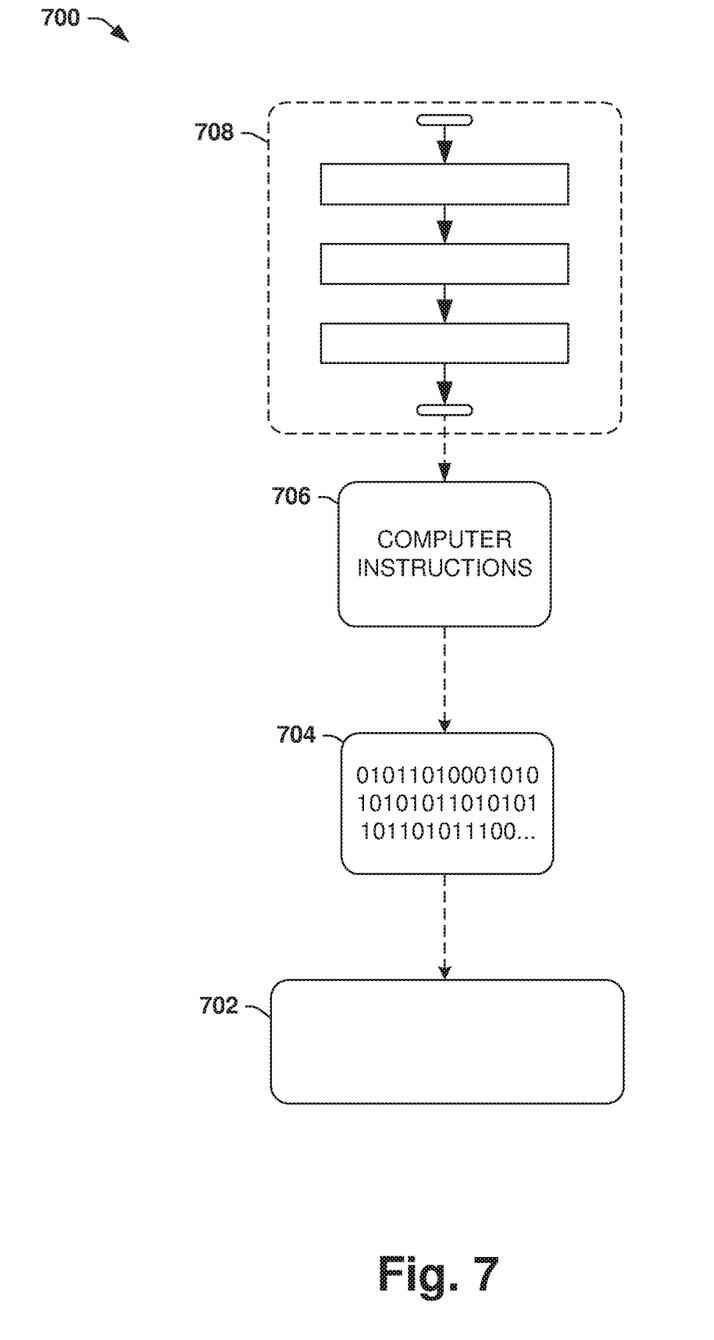
FIG. 7 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein. An example computer-readable medium that may be devised in these ways is illustrated in FIG. 7, wherein the embodiment 700 comprises a computer-readable medium 702 (e.g., a flash drive, CD-R, DVD-R, application-specific integrated circuit (ASIC), field-programmable gate array (FPGA), a platter of a hard disk drive, etc.), on which is encoded computer-readable data 704. This computer-readable data 704 in turn comprises a set of processor-executable instructions 706 configured to operate according to one or more of the principles set forth herein. In one such embodiment 700, the processor-executable instructions 706 may be configured to perform a method 708, such as at least some of the example method 600 of FIG. 6, for example. In another such embodiment, the processor-executable instructions 706 may be configured to implement a system, such as at least some of the exemplary systems FIGS. 1 and 4, respectively, for example. Many such computer-readable media may be devised by those of ordinary skill in the art that are configured to operate in accordance with one or more of the techniques presented herein.

Moreover, the words "example" and/or "exemplary" are used herein to mean serving as an example, instance, or illustration. Any aspect, design, etc. described herein as "example" and/or "exemplary" is not necessarily to be construed as advantageous over other aspects, designs, etc. Rather, use of these terms is intended to present concepts in a concrete fashion. As used in the present disclosure, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in the present disclosure and the appended claims may generally be construed to mean "one or more" unless specified otherwise or clear from context to be directed to a singular form. Also, at least one of A and B or the like generally means A or B or both A and B.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used in the present disclosure, the terms "component," "module," "system," "interface," and the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

Further, unless specified otherwise, "first," "second," and/or the like are not intended to imply a temporal aspect, a spatial aspect, an ordering, etc. Rather, such terms are merely used as identifiers, names, etc. for features, elements, items, etc. (e.g., "a first channel and a second channel" generally corresponds to "channel A and channel B" or two different (or identical) channels).

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component that performs the specified function of the described component (e.g., that is functionally equivalent), even though not structurally equivalent to the disclosed structure, which performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes," "having," "has," "with," or variants thereof are used in either the detailed description or the claims, such terms are intended to be inclusive in a manner similar to the term "comprising."

What is claimed is:

1. A system for an imaging modality, comprising:
a radiation source configured to emit radiation;
a detector array configured to detect the radiation emitted by the radiation source, the detector array comprising a plurality of charge integrating channels, the charge integrating channels being configured to generate a signal; and
a channel combining component configured to combine information generated by at least some of the plurality of charge integrating channels to generate one or more virtual channels, wherein the one or more virtual channels represent at least two charge integrating channels.

2. The system of claim 1, wherein the channel combining component combines information generated by at least 10 charge integrating channels to create a first virtual channel.

3. The system of claim 1, the channel combining component configured to weight information generated by a first charge integrating channel during an acquisition view differently than information generated by a second charge integrating channel during the acquisition view when combining the information generated by the first charge integrating channel with the information generated by the second charge integrating channel to generate a first virtual channel.

4. The system of claim 1, the channel combining component configured to generate at least a first virtual channel and a second virtual channel, the first and second virtual channels being respectively indicative of information yielded, during a first acquisition view, from at least one charge integrating channel in common between the first and second virtual channels.

5. The system of claim 1, the channel combining component configured to generate at least a first virtual channel and a second virtual channel, the first virtual channel indicative of information yielded from a first number of charge integrating channels and the second virtual channel indicative of information yielded from a second number of charge integrating channels, the first number of charge integrating channels being different than the second number of charge integrating channels.

6. The system of claim 1, a number of charge integrating channels represented by respective virtual channels being a function of at least one of:
a location of the virtual channel relative to a center of the detector array;
an amount of radiation emitted by the radiation source;
an amount of radiation detected by the detector array; and
an acquisition view to which the respective virtual channels are related.

7. The system of claim 1, a first virtual channel representing a different number of charge integrating channels than a second virtual channel in a same acquisition view.

8. The system of claim 1, the channel combining component configured to generate a first virtual channel having a first location relative to a center of the detector array and configured to shift the first virtual channel such that, once shifted, the first virtual channel has a second location relative to the center of the detector array.

9. The system of claim 1, the radiation source comprising an ionizing radiation source.

10. The system of claim 1, the imaging modality comprising a CT imaging modality.

11. A method for generating virtual channels in an imaging modality, comprising:
generating information from respective charge integrating channels of a detector array, the generated information indicative of radiation detected by respective charge integrating channels of the detector array; and
generating a first virtual channel representing two or more of the charge integrating channels based at least in part upon the generated information.

12. The method of claim 11, comprising, generating a second virtual channel representing two or more of the charge integrating channels, the first and second virtual channels representing at least one charge integrating channel that is common to the first and second virtual channels.

13. The method of claim 12, the first and second virtual channels being indicative of information yielded from a substantially similar acquisition view.

14. The method of claim 11, comprising adjusting a size of the first virtual channel by altering a number of charge integrating channels represented by the first virtual channel.

15. The method of claim 14, comprising altering the number of charge integrating channels represented by the first virtual channel based at least in part upon at least one of:
a location on the detector array to which the first virtual channel corresponds;
an amount of radiation detected by the detector array; and
a dose applied by a radiation source.

16. The method of claim 11, generating the first virtual channel comprising generating the first virtual channel representing information yielded from at least first and second charge integrating channels during a first interval of time, and the method comprising:
generating a second virtual channel representing information yielded from at least one of the first and second charge integrating channels during a second interval of time, the second interval of time substantially corresponding to the first interval of time.

17. The method of claim 11, the first virtual channel having an effective channel position, and the method comprising adjusting the effective channel position of the first virtual channel.

18. The method of claim 11, generating the first virtual channel comprising:
- weighting generated information from a first charge integrating channel;
- weighting generated information from a second charge integrating channel; and
- combining the weighted information from the first charge integrating channel with the weighted information from the second charge integrating channel to generate the first virtual channel.

19. The method of claim 18, the first charge integrating channel weighted differently than the second charge integrating channel.

20. A non-transitory computer-readable medium comprising computer executable instructions that, when executed via a processing unit of a computing system, causes the computing system to perform a method, the method comprising:
- generating information from respective charge integrating channels of a detector array, the generated information indicative of radiation detected by respective charge integrating channels of the detector array; and
- generating a first virtual channel representing two or more of the charge integrating channels based at least in part upon the generated information.

\* \* \* \* \*